US012036525B2

(12) United States Patent
Thomas et al.

(10) Patent No.: US 12,036,525 B2
(45) Date of Patent: Jul. 16, 2024

(54) GAS MICRO REACTOR UTILIZING MEMBRANE PACKAGING

(71) Applicant: Selective Micro Technologies, LLC, Dublin, OH (US)

(72) Inventors: Jeff Thomas, Plain City, OH (US); Tanja Miller, Delaware, OH (US)

(73) Assignee: Selective Micro Technologies, LLC, Dublin, OH (US)

( * ) Notice: Subject to any disclaimer, the term of this patent is extended or adjusted under 35 U.S.C. 154(b) by 0 days.

(21) Appl. No.: 17/512,118

(22) Filed: Oct. 27, 2021

(65) Prior Publication Data

US 2022/0126254 A1    Apr. 28, 2022

Related U.S. Application Data

(60) Provisional application No. 63/106,115, filed on Oct. 27, 2020.

(51) Int. Cl.
*B01J 19/00*      (2006.01)
*B01J 19/24*      (2006.01)

(52) U.S. Cl.
CPC ....... *B01J 19/0093* (2013.01); *B01J 19/2475* (2013.01); *B01J 2219/00833* (2013.01);
(Continued)

(58) Field of Classification Search
CPC . A23L 3/00; A23L 3/34; A23L 3/3409; A23L 3/34095; A61L 2/00; A61L 2/16; A61L 2/20; B01J 7/00; B01J 7/02; B01J 19/00; B01J 19/0093; B01J 19/02; B01J 19/08; B01J 19/12; B01J 19/122; B01J 19/129;
B01J 19/14; B01J 19/24; B01J 19/2445; B01J 19/2475; B01J 2219/00; B01J 2219/00781; B01J 2219/00819; B01J 2219/00833; B01J 2219/00844;
(Continued)

(56) References Cited

U.S. PATENT DOCUMENTS 2,022,262 A    11/1935   White
2,071,091 A    2/1937    Taylor
(Continued)

FOREIGN PATENT DOCUMENTS

CA         959238 A    12/1974
CN        1104610 A     7/1995
(Continued)

OTHER PUBLICATIONS

Simpson et al., A Focus on Chlorine Dioxide: The "Ideal" Biocide. Retrieved online at: https://www.asminternational.org/search/-/journal_content/56/33542825/434102/PUBLICATION-CONFERENCEPAPER-TEMPLATE. 20 pages, Dec. 31, 1993.
(Continued)

*Primary Examiner* — Natasha E Young
(74) *Attorney, Agent, or Firm* — McCarter & English, LLP

(57) ABSTRACT

Apparatuses for generation of a gas, for example chlorine dioxide, methods of forming an apparatus, and methods of use thereof are provided. The apparatus may include at least one pouch composed of a hydrophobic material and a reactant disposed within the interior of the pouch. The reactant generates a desired gas in the presence of an initiating agent.

26 Claims, 12 Drawing Sheets

(52) U.S. Cl.
CPC ........... *B01J 2219/00844* (2013.01); *B01J 2219/00864* (2013.01); *B01J 2219/00907* (2013.01)

(58) Field of Classification Search
CPC .... B01J 2219/00851; B01J 2219/00858; B01J 2219/00864; B01J 2219/00905; B01J 2219/00907; B01J 2219/02; B01J 2219/025; B01J 2219/0295; C01B 11/00; C01B 11/02; C01B 11/022
See application file for complete search history.

(56) References Cited

U.S. PATENT DOCUMENTS

| | | |
|---|---|---|
| 2,071,094 A | 2/1937 | Vincent |
| 2,323,593 A | 7/1943 | Hampel et al. |
| 2,482,891 A | 9/1949 | Aston |
| 3,183,057 A | 5/1965 | Marks et al. |
| 3,332,548 A | 7/1967 | Piazze et al. |
| 3,591,515 A | 7/1971 | Lovely |
| 3,695,839 A | 10/1972 | Callerame |
| 3,754,079 A | 8/1973 | Callerame |
| 3,915,212 A | 10/1975 | Bujan et al. |
| 3,950,158 A | 4/1976 | Gossett |
| 4,055,672 A | 10/1977 | Hirsch et al. |
| 4,094,119 A | 6/1978 | Sullivan |
| 4,200,610 A | 4/1980 | Swaine et al. |
| 4,528,228 A | 7/1985 | Clevenger |
| 4,542,539 A | 9/1985 | Rowe, Jr. et al. |
| 4,547,381 A | 10/1985 | Mason et al. |
| 4,585,482 A | 4/1986 | Tice et al. |
| 4,596,713 A | 6/1986 | Burdette |
| 4,597,218 A | 7/1986 | Friemel et al. |
| 4,605,165 A | 8/1986 | Van Loveren et al. |
| 4,613,544 A | 9/1986 | Burleigh |
| 4,679,706 A | 7/1987 | Magid et al. |
| 4,683,039 A | 7/1987 | Twardowski et al. |
| 4,689,169 A | 8/1987 | Mason et al. |
| 4,689,215 A | 8/1987 | Ratcliff |
| 4,696,811 A | 9/1987 | Ratcliff |
| 4,748,904 A | 6/1988 | Razeto et al. |
| 4,758,239 A | 7/1988 | Yeo et al. |
| 4,788,053 A | 11/1988 | Ratcliff |
| 4,792,442 A | 12/1988 | Ratcliff |
| 4,808,389 A | 2/1989 | Ratcliff |
| 4,818,519 A | 4/1989 | Ratcliff |
| 4,828,772 A | 5/1989 | Lopatin et al. |
| 4,837,009 A | 6/1989 | Ractliff |
| 4,851,213 A | 7/1989 | Ratcliff |
| 4,886,657 A | 12/1989 | Ratcliff |
| 4,889,714 A | 12/1989 | Ratcliff |
| 4,923,753 A | 5/1990 | Walles et al. |
| 4,925,645 A | 5/1990 | Mason |
| 4,925,656 A | 5/1990 | Ratcliff |
| 4,932,155 A | 6/1990 | Friemel et al. |
| 4,994,056 A | 2/1991 | Ikeda |
| 5,009,875 A | 4/1991 | Kelley et al. |
| 5,091,107 A | 2/1992 | Hutchings |
| 5,093,097 A | 3/1992 | Engstrom et al. |
| 5,126,070 A | 6/1992 | Leifheit et al. |
| 5,165,910 A | 11/1992 | Oikawa et al. |
| 5,200,171 A | 4/1993 | Ratcliff |
| 5,267,646 A | 12/1993 | Inoue et al. |
| 5,342,601 A | 8/1994 | Cawlfield et al. |
| 5,346,061 A | 9/1994 | Newman et al. |
| 5,354,932 A | 10/1994 | Bhattacharyya et al. |
| 5,360,609 A | 11/1994 | Wellinghoff |
| 5,380,517 A | 1/1995 | Sokol |
| 5,380,518 A | 1/1995 | Roozdar |
| 5,416,141 A | 5/1995 | Endres et al. |
| 5,441,345 A | 8/1995 | Garvey et al. |
| 5,458,244 A | 10/1995 | Emori |
| 5,486,344 A | 1/1996 | Winters et al. |
| 5,489,435 A | 2/1996 | Ratcliff |
| 5,523,118 A | 6/1996 | Williams |
| 5,545,389 A | 8/1996 | Winters et al. |
| 5,567,405 A | 10/1996 | Klatte et al. |
| 5,573,743 A | 11/1996 | Klatte et al. |
| 5,631,300 A | 5/1997 | Wellinghoff |
| 5,650,446 A | 7/1997 | Wellinghoff et al. |
| 5,690,672 A | 11/1997 | Cohen |
| 5,705,092 A | 1/1998 | Wellinghoff et al. |
| 5,707,739 A | 1/1998 | Wellinghoff et al. |
| 5,711,211 A | 1/1998 | Ide et al. |
| 5,719,100 A | 2/1998 | Zahradnik et al. |
| 5,730,948 A | 3/1998 | Klatte et al. |
| 5,770,171 A | 6/1998 | Sundblad et al. |
| 5,776,374 A | 7/1998 | Newsham et al. |
| 5,811,115 A | 9/1998 | Ratcliff |
| 5,834,003 A | 11/1998 | Ratcliff |
| 5,851,374 A | 12/1998 | Cowley et al. |
| 5,853,085 A | 12/1998 | Luttrell |
| 5,853,689 A | 12/1998 | Klatte |
| RE36,064 E | 1/1999 | Davidson et al. |
| 5,855,861 A | 1/1999 | Lee |
| 5,856,085 A | 1/1999 | Wang et al. |
| 5,858,322 A | 1/1999 | Gray |
| 5,879,378 A | 3/1999 | Usui |
| 5,885,543 A | 3/1999 | Klatte |
| 5,891,838 A | 4/1999 | Angell et al. |
| 5,895,638 A | 4/1999 | Tenney |
| 5,922,776 A | 7/1999 | Wellinghoff et al. |
| 5,965,004 A | 10/1999 | Cowley et al. |
| 5,965,264 A | 10/1999 | Barenberg et al. |
| 5,968,454 A | 10/1999 | Deacon et al. |
| 5,972,238 A | 10/1999 | Rimpler et al. |
| 5,974,810 A | 11/1999 | Speronello |
| 5,980,826 A | 11/1999 | Barenberg et al. |
| 6,000,848 A | 12/1999 | Massioui |
| 6,033,704 A | 3/2000 | Talley |
| 6,046,243 A | 4/2000 | Wellinghoff et al. |
| 6,077,495 A | 6/2000 | Speronello et al. |
| 6,132,748 A | 10/2000 | Khanna et al. |
| 6,174,508 B1 | 1/2001 | Klatte |
| 6,238,643 B1 | 5/2001 | Thangaraj et al. |
| 6,363,734 B1 | 4/2002 | Aoyagi |
| 6,376,032 B1 | 4/2002 | Clarke et al. |
| 6,602,466 B2 | 8/2003 | Hamilton et al. |
| 6,607,696 B1 | 8/2003 | Hamilton et al. |
| 7,922,984 B2 | 4/2011 | Hamilton et al. |
| 8,512,671 B2 * | 8/2013 | Nosznicius .......... C01B 11/028 422/240 |
| 2001/0012504 A1 | 8/2001 | Thangaraj et al. |
| 2003/0180384 A1 | 9/2003 | Koermer et al. |
| 2006/0039840 A1 | 2/2006 | Chia et al. |
| 2006/0120945 A1 | 6/2006 | Warner et al. |
| 2022/0226527 A1 | 7/2022 | Thomas |

FOREIGN PATENT DOCUMENTS

| | | | |
|---|---|---|---|
| EP | 0230737 A1 | 8/1987 | |
| EP | 0423817 A2 | 4/1991 | |
| EP | 0571228 A2 | 11/1993 | |
| EP | 0581550 A1 | 2/1994 | |
| EP | 0611162 A1 | 8/1994 | |
| EP | 0611163 A1 | 8/1994 | |
| FR | 2555552 A1 | 5/1985 | |
| JP | 1-71804 U | 5/1989 | |
| JP | 2-55201 A | 2/1990 | |
| JP | 4-75554 | 3/1992 | |
| WO | 1994/25263 A1 | 11/1994 | |
| WO | 1998/38865 A1 | 9/1998 | |
| WO | 1999/19001 A2 | 4/1999 | |
| WO | 1999/24356 A1 | 5/1999 | |
| WO | 2000/10695 A1 | 3/2000 | |
| WO | 2000/21879 A1 | 4/2000 | |
| WO | 2000/32052 A1 | 6/2000 | |
| WO | 2001/33961 A1 | 5/2001 | |
| WO | 2001/60750 A2 | 8/2001 | |
| WO | 2002/00332 A1 | 1/2002 | |
| WO | WO-03051407 A1 * | 6/2003 | ............... A61L 2/20 |

(56) References Cited

FOREIGN PATENT DOCUMENTS

WO     WO-2004073755 A1 *   9/2004  ............... A61L 2/20
WO     2011/160104 A2    12/2011

OTHER PUBLICATIONS

European Office Action for Application No. 01916105.8, dated Feb. 10, 2008, 4 pages.
European Office Action for Application No. 02805178.7, dated Jun. 5, 2007, 4 pages.
International Search Report and Written Opinion for Application No. PCT/US2021/056868, dated Feb. 3, 2022, 14 pages.
International Preliminary Report on Patentability for Application No. PCT/US2021/056868, dated May 2, 2023, 9 pages.

* cited by examiner

See Detail "A"

GAS MICRO REACTOR UTILIZING MEMBRANE PACKAGING

This application claims priority under 35 U.S.C. § 119 to U.S. Provisional Application No. 63/106,155, which was filed on Oct. 27, 2020. The entire contents of the aforementioned application are incorporated herein by reference in its entirety.

The present disclosure relates to an apparatus for generating a gas. In some embodiments, the generated gas is chlorine dioxide, carbon dioxide, oxygen, nitrogen, argon, helium, calcium carbonate, or a combination thereof. More particularly, the present disclosure is directed to at least one pouch containing a reactant that generates a gas in the presence of an initiating agent.

Sterilizing gases such as chlorine dioxide are useful disinfectants in many industries. For example, chlorine dioxide can be used to wash meat and food products to remove food borne pathogens and to prolong shelf line. Chlorine dioxide can also be used to sterilize high traffic areas such as hotels, hospitals, livery vehicles, veterinary clinics, restaurants, office buildings, municipal buildings, schools, and the like.

Use of chlorine dioxide can prompt health concerns. For example, chlorine dioxide that is improperly generated or stored can be explosive or ignite.

Therefore, there exists an unmet need for the safe and effective generation of gases such as chlorine dioxide. Accordingly, the present disclosure provides for an apparatus for generating gases such as chlorine dioxide, methods of forming the apparatus, and methods of use thereof.

The present disclosure provides various embodiments of an apparatus for generation of a gas. The apparatus includes at least one pouch, each pouch comprising a hydrophobic material, and a reactant disposed within an interior of at least one pouch and in direct contact with an interior lining of at least one pouch. The reactant generates the gas in the presence of an initiating agent.

In some embodiments, the hydrophobic material is polytetrafluoroethylene. In some embodiments, the hydrophobic material includes pores sized between 0.05 micrometers and 1.00 micrometers. In some embodiments, the hydrophobic material possesses a bubble point ranging between 20 psi and 30 psi.

In some embodiments, the initiating agent is a vapor. In further embodiments, the initiating agent is water vapor. In some embodiments, the reactant is a solid. In some embodiments, the reactant comprises a combination of sodium chloride and citric acid. In some embodiments, the reactant fills between 20-60% of the interior of each pouch.

In some embodiments, the hydrophobic material is configured to allow release of the gas out of each pouch. In some embodiments, the hydrophobic material is configured to allow entry of the initiating agent into the interior of each pouch. In some embodiments, the interior of the pouch consists of the reactant and air.

In some embodiments, the generated gas is chlorine dioxide, carbon dioxide, oxygen, nitrogen, argon, helium, calcium carbonate, or a combination thereof.

In some embodiments, the apparatus further includes multiple pouches connected in a manner that allows for removal of one pouch from the multiple pouches by cutting away the one pouch. In further embodiments, each pouch comprises a single layer of the hydrophobic material.

The present disclosure provides various embodiments of a method of forming an apparatus for generation of a gas. The method includes providing at least two pouches including a hydrophobic material, each pouch including an interior, and a reactant disposed within each interior, wherein the reactant generates the gas in the presence of an initiating agent; and connecting the at least two pouches at a perimeter of each pouch, each pouch spaced from one another such that one pouch is removable from the at least two pouches by cutting away the one pouch.

In some embodiments, the at least two pouches are connected by heat sealing or stamping the perimeter of each pouch. In some embodiments, the hydrophobic material is polytetrafluoroethylene. In some embodiments, the hydrophobic material includes pores sized between 0.05 micrometers and 1.00 micrometers. In some embodiments, the hydrophobic material possesses a bubble point ranging between 20 psi and 30 psi.

In some embodiments, the initiating agent is a vapor. In further embodiments, the initiating agent is water vapor. In some embodiments, the reactant is a solid. In some embodiments, the reactant comprises a combination of sodium chloride and citric acid. In some embodiments, the reactant fills between 20-60% of the interior of each pouch.

In some embodiments, the hydrophobic material is configured to allow release of the gas out of each pouch. In some embodiments, the hydrophobic material is configured to allow entry of the initiating agent into the interior of each pouch. In some embodiments, the interior of the pouch consists of the reactant and air. In some embodiments, the generated gas is chlorine dioxide. In some embodiments, each pouch includes a single layer of the hydrophobic material.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Similarly, the use of the term "comprising," as well as other forms, such as "comprises," is also not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The disclosed apparatus provides an apparatus for generating a gas, for example chlorine dioxide. The apparatus includes a durable pouch that safely houses a reactant and is configured to permit the introduction of an initiating agent from outside the pouch. The porous pouch material is also configured to allow the release of the generated gas out of the apparatus.

Figure 1:
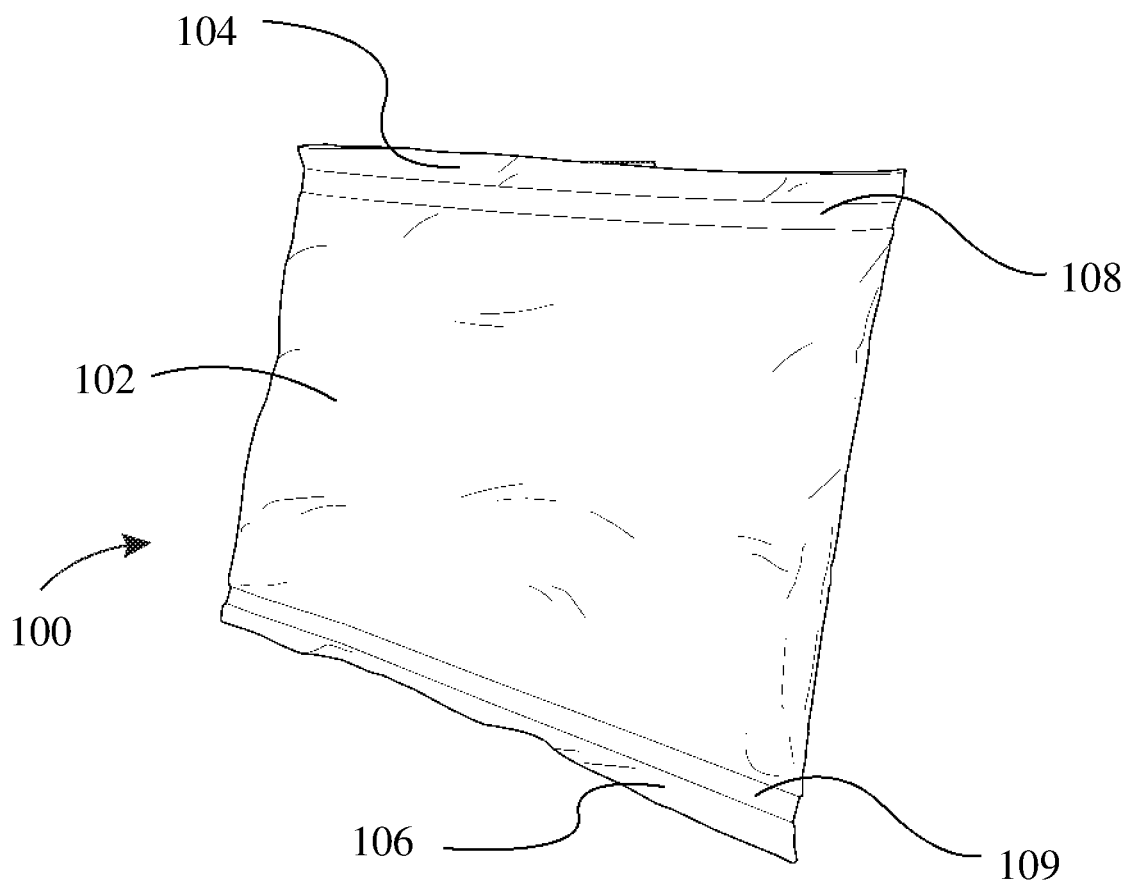
FIG. 1 is an outer view of a pouch for generating a gas, according to some embodiments.

In some embodiments, the apparatus 100 includes a pouch 102 for generating a gas. FIG. 1 is an outer view of the pouch 102, according to some embodiments. The pouch 102 is composed of a hydrophobic material. For example, the pouch 102 may be composed of polytetrafluoroethylene (PTFE). PTFE offers advantages compared to other possible pouch 102 materials. Specifically, PTFE is more robust due to its high hydrophobicity and does not become embrittled during gas generation. In some embodiments, the pouch 102 is composed of a single layer of hydrophobic material.

In some embodiments, the hydrophobic material is porous. In further embodiments, the pores may be sized between 0.01 micrometers and 3.00 micrometers, between 0.03 micrometers and 2.00 micrometers, between 0.05 micrometers and 1.00 micrometers, or any range in between. In some embodiments, the pores are sized between 0.2 nanometers and 0.4 nanometers or any range in between. The pores are of suitable size to allow passage of an initiating agent and a generated gas through the pouch 102 material.

In some embodiments, the hydrophobic material possesses a bubble point ranging between 10 psi and 50 psi, between 15 psi and 25 psi, between 20 psi and 30 psi, or any range in between.

The pouch 102 may include a sealed perimeter 104. The perimeter 104 may be stamped or heat sealed. In some embodiments, the pouch 102 may be tear-drop shaped, or any shape suitable for containing a reactant.

Figure 2:
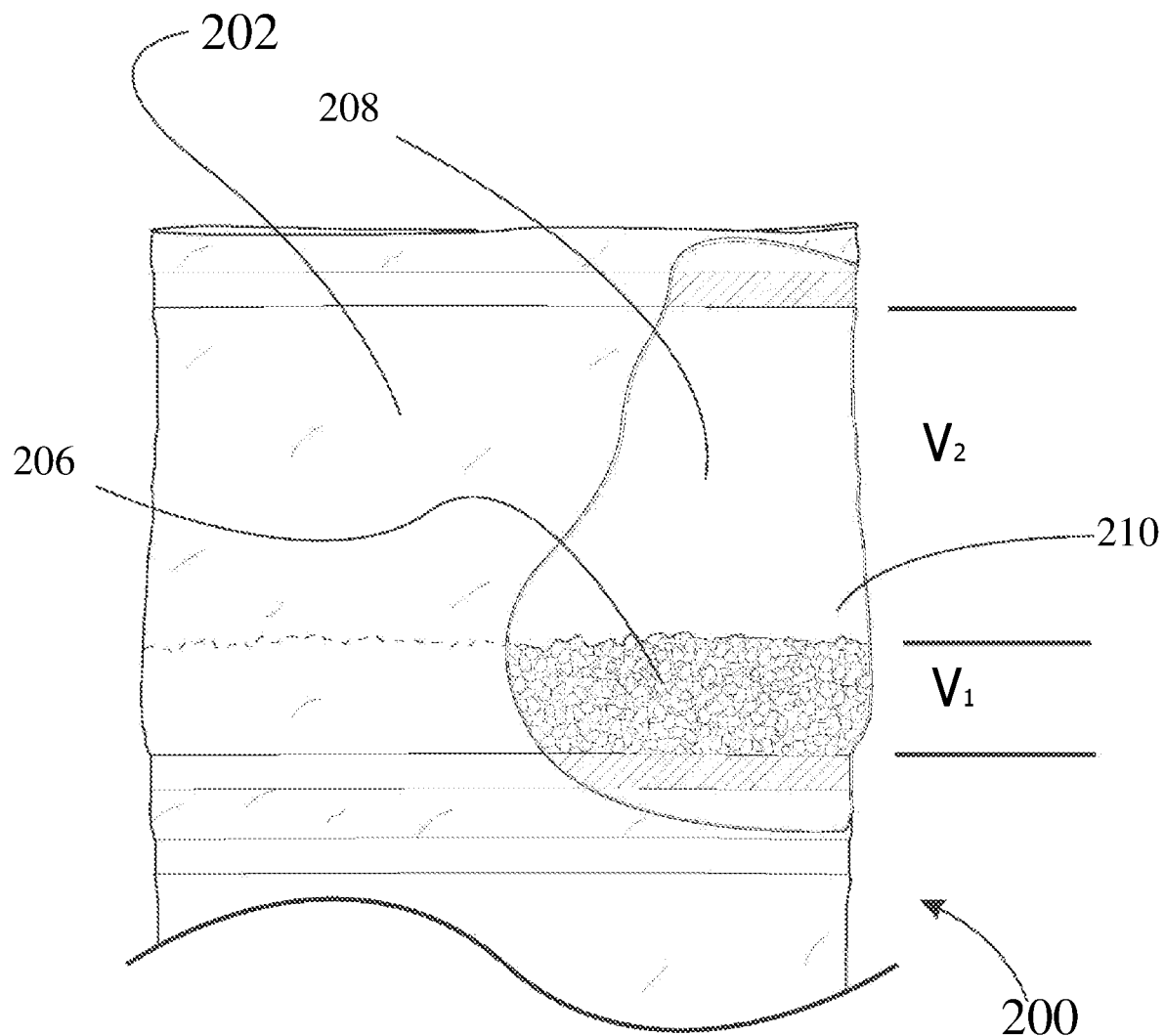
FIG. 2 is an inner view of a pouch for generating a gas, according to some embodiments.

FIG. 2 is an inner view of a pouch 102 for generating a gas, according to some embodiments. The apparatus 100 may further include a reactant 206 disposed within an interior of each pouch 102 and in direct contact with an interior lining of each pouch 102. The reactant 206 generates the desired gas in the presence of an initiating agent.

In some embodiments, the initiating agent is a vapor. For example, the initiating agent may be water vapor. In such embodiments, the pouch 102 is comprised of a material with sufficient porosity to allow the passage of water vapor into the interior of the pouch 102. For example, PTFE is sufficiently porous to admit water vapor yet its hydrophobicity will prevent the vapor from being absorbed by the pouch 102 itself.

In some embodiments, the water vapor is provided in a separate pouch. Such embodiments are described in detail with regards to FIGS. 17 and 18. In some embodiments, the water vapor is provided by surrounding air. Such embodiments are described in detail with regards to FIGS. 13-16.

In some embodiments, reactant 206 is provided in solid form. Selection of reactant 206 determines the gas that will be generated by the apparatus 100. For example, a reactant composed of a combination of sodium chloride and citric acid would generate chlorine dioxide in the presence of water vapor. Reactants may also be chosen to generate chlorine dioxide, carbon dioxide, oxygen, nitrogen, argon, helium, calcium carbonate, or a combination thereof. In some embodiments, a combination of carbon dioxide and chlorine dioxide is generated.

In some embodiments, the reactant 206 fills a portion of the interior 210 of the pouch 102. For example, reactant 206 may fill a volume $V_1$ that is between 10-90%, 20-60%, 30-50%, or any percentage in between, of the interior of each pouch 102. The volume $V_2$ of the interior of the pouch 102 that is not filled with reactant 206 contains air 208.

Figure 3:
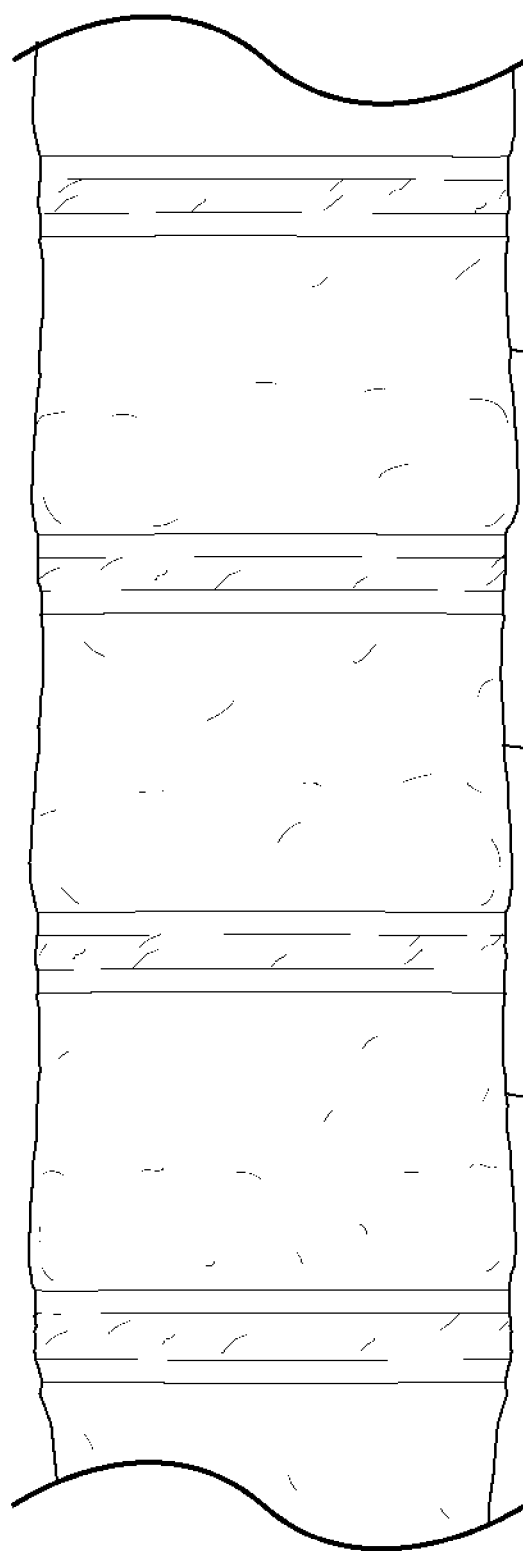
FIG. 3 is an outer front view of multiple pouches connected in succession, according to some embodiments.
Figure 4:
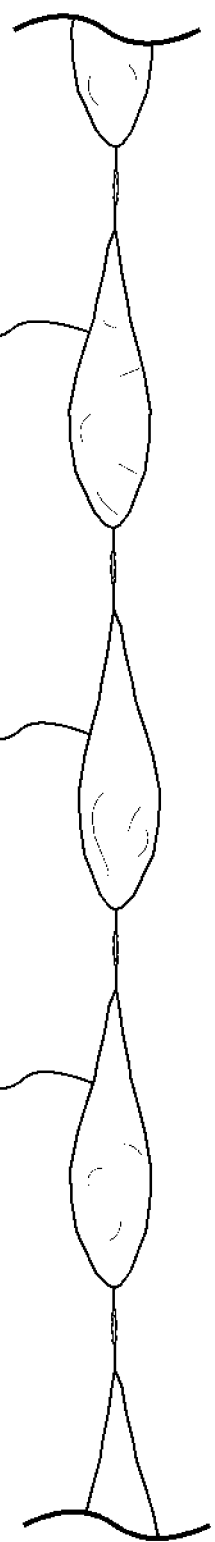
FIG. 4 is a side view of the multiple pouches depicted in FIG. 3.

FIG. 3 is an outer front view of multiple pouches 302, 302', and 302" connected in succession, according to some embodiments. FIG. 4 is a side view of the multiple pouches depicted in FIG. 3. The multiple pouches 302, 302', and 302" may be connected in a manner that allows for removal of one pouch from the multiple pouches by cutting away the one pouch at a perimeter 304 of the pouch. Although three pouches are depicted in FIG. 3, the apparatus may include any number of pouches.

The pouches may be connected at their perimeter 304 and spaced from one another such that one pouch is removable from the other pouches by cutting away the one pouch. For example, pouch 302 may be cut away from pouches 302' and 302" at perimeter 304. In some embodiments, the perimeter 304 between two pouches is heat sealed or stamped.

A method of producing the apparatus of FIG. 3 includes providing at least two pouches holding the reactant. The pouches are connected at their perimeters. In some embodiments, the pouches are connected in succession. In other words, each pouch is connected to no more than two other pouches, except for each pouch at the ends of the apparatus. Each pouch is spaced from one another such that one pouch is removable from the other pouches by cutting away the one pouch.

Figure 5:
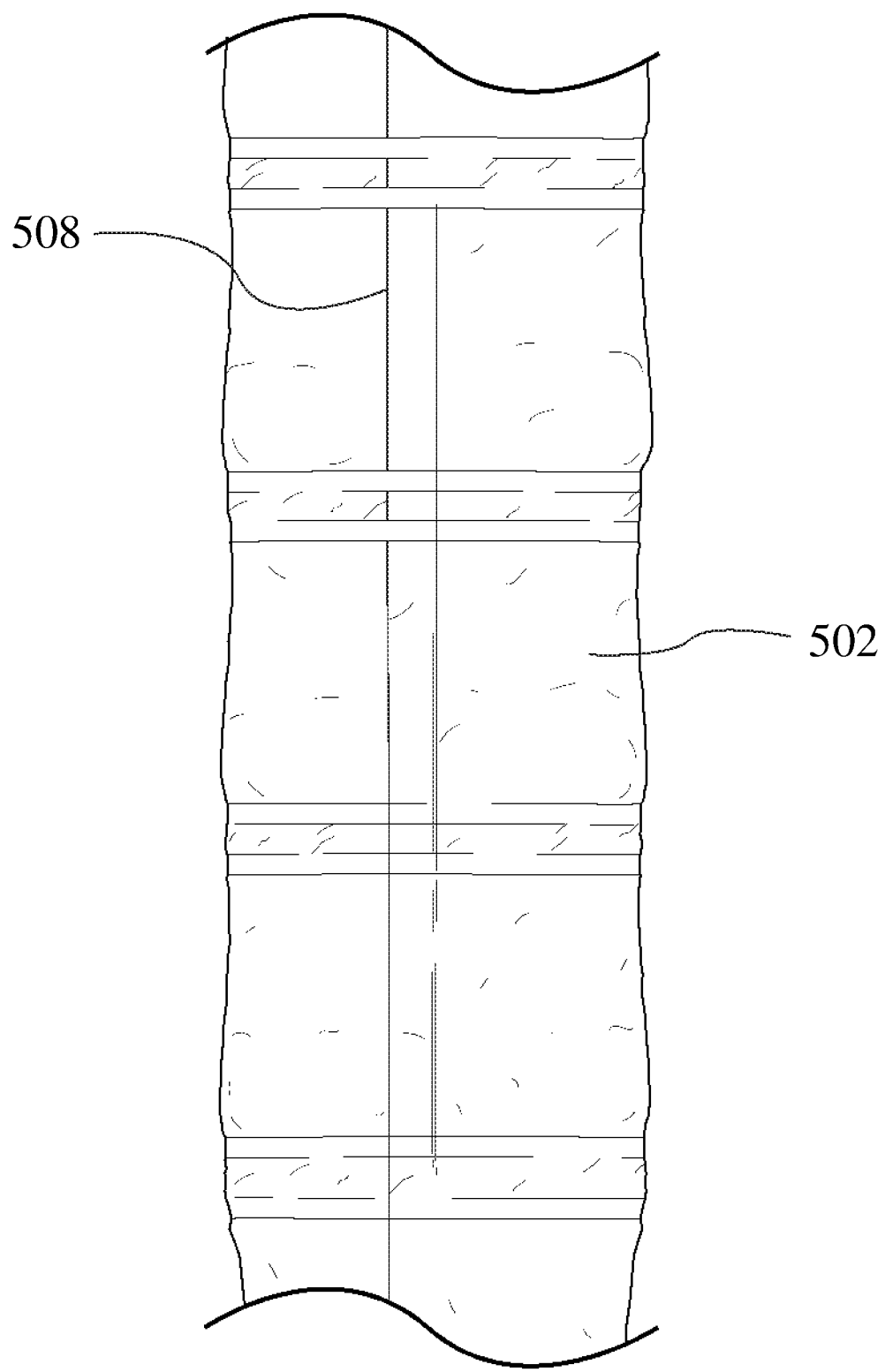
FIG. 5 is an outer front view of multiple pouches connected in succession with a sachet, according to some embodiments.

FIG. 5 is an outer front view of multiple pouches connected in succession with a vertical sachet 508, according to some embodiments. The sachet 508 may contain the reactant within each pouch. The sachet 508 is composed of a material that allows an initiating agent into the sachet 508 and allows for a generated gas to leave the sachet 508. In some embodiments, the sachet 508 may be composed of the same material as the pouch 102.

In some embodiments, the sachet 508 runs continuously through each pouch. In other embodiments, each pouch contains an individual sachet that contains the reactant.

Figure 6:
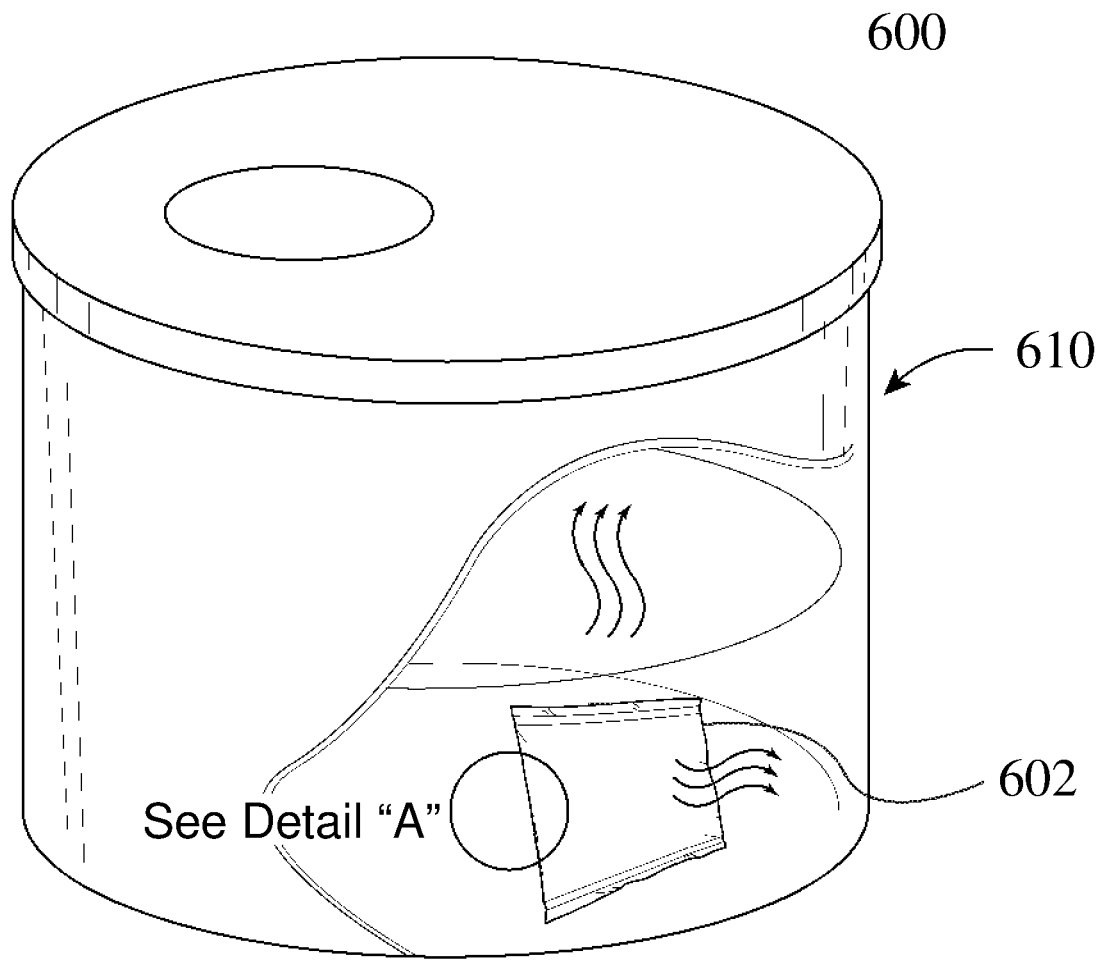
FIG. 6 is a cutaway view of a canister housing a pouch for generating a gas, according to some embodiments.

FIG. 6 is a cutaway view of a canister 610 housing a pouch 602 for generating a gas, according to some embodiments. The canister 610 may include one or more layers, each layer housing at least one pouch 602. The gas generated from each pouch 602 may be accumulated within the canister 610. A user can open or vent the canister 610 to collect the released gas.

In embodiments wherein the initiating agent is water vapor, the canister 610 may be configured to receive water. The canister 610 may be configured to heat stored water to create water vapor. The canister 610 may be further configured to expose one or more pouches 602 within the canister 610 to the created water vapor.

Figure 7:
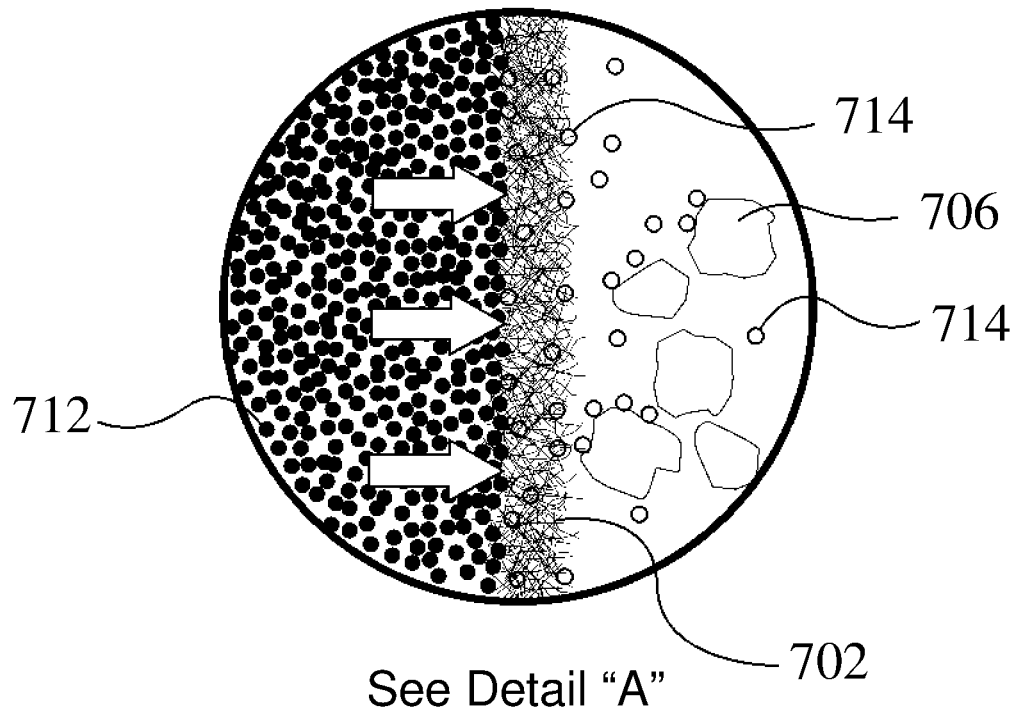
FIG. 7 is a mock-up microscopic view of an initiating agent entering a pouch containing a reactant, according to some embodiments.

FIG. 7 is a mock-up microscopic view of an initiating agent 712 entering a pouch 702 containing a reactant 706, according to some embodiments. As illustrated, the pouch 702 is composed of a sufficiently porous material to allow the passage of the initiating agent 712, for example water vapor. The initiating agent 712 then interacts with the reactant 706 to generate a gas.

Figure 8:
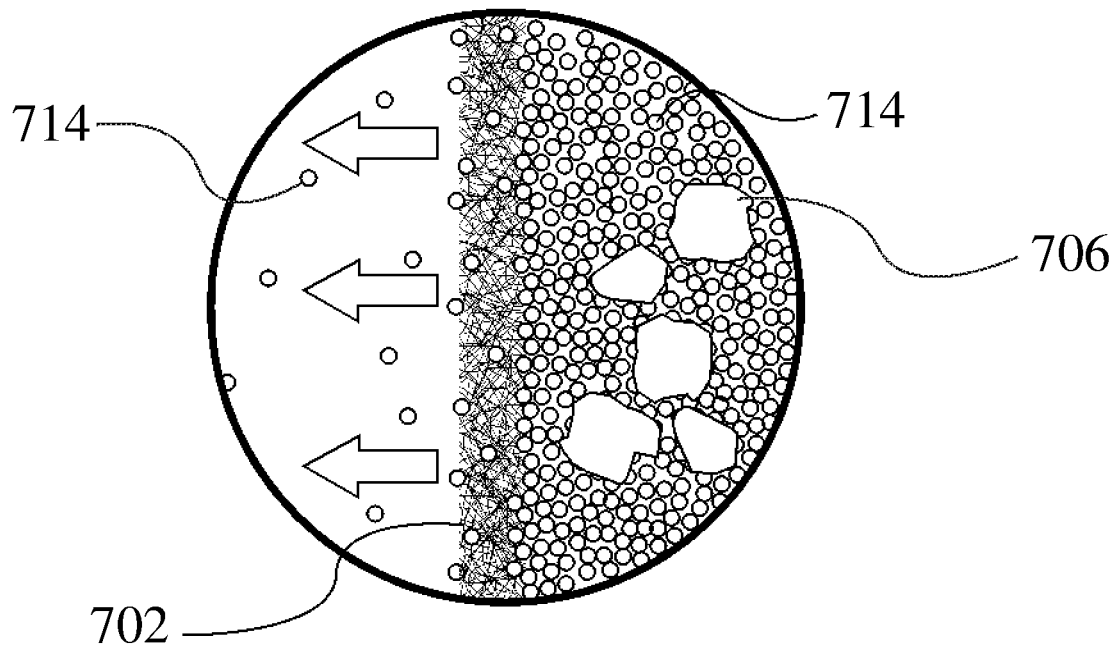
FIG. 8 is a mock-up microscopic view of a generated gas exiting a pouch containing a reactant, according to some embodiments.

FIG. 8 is a mock-up microscopic view of a generated gas 714 exiting a pouch 702 containing a reactant 706, according to some embodiments. As illustrated, the pouch 702 is composed of a sufficiently porous material to allow the passage of the generated gas 714, for example chlorine dioxide, carbon dioxide, oxygen, nitrogen, argon, helium, calcium carbonate, or a combination thereof. In some embodiments, a combination of carbon dioxide and chlorine dioxide is generated.

Figure 9:
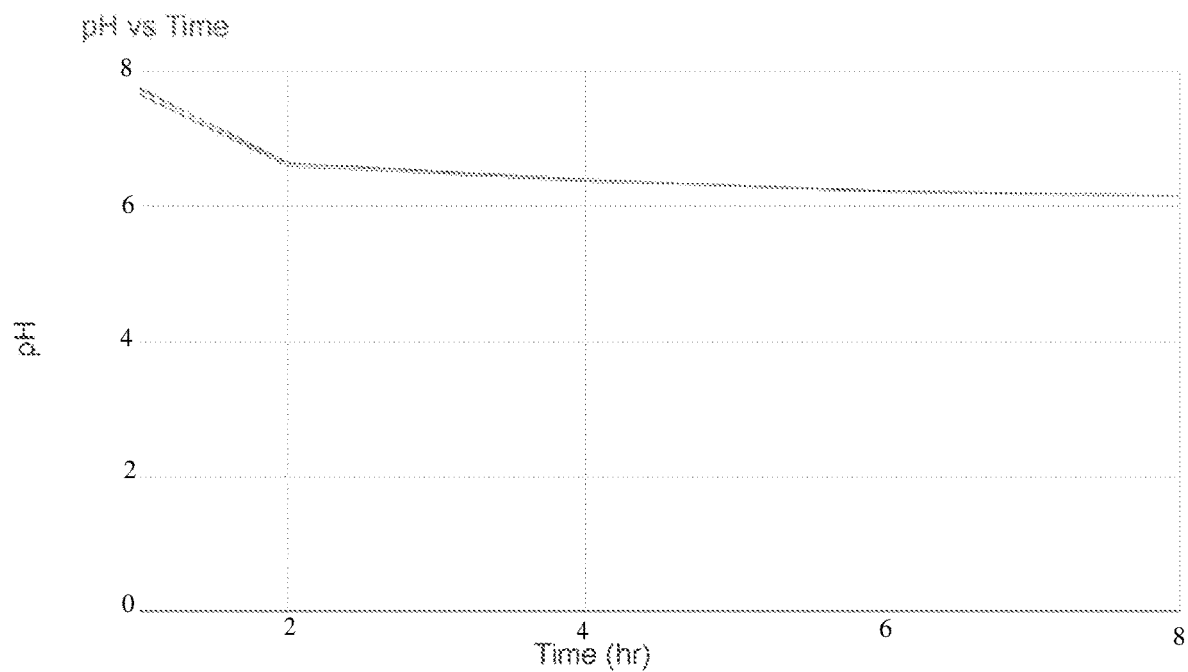
FIG. 9 is a graph depicting the pH of a generated chlorine dioxide solution over time.

FIG. 9 is a graph depicting the pH of a generated chlorine dioxide solution over time. Typically chlorine dioxide solutions become acidic quickly. However, the release of chlorine dioxide through the membrane of the above described devices keeps the pH of the solution close to a neutral 7.

Figure 10:
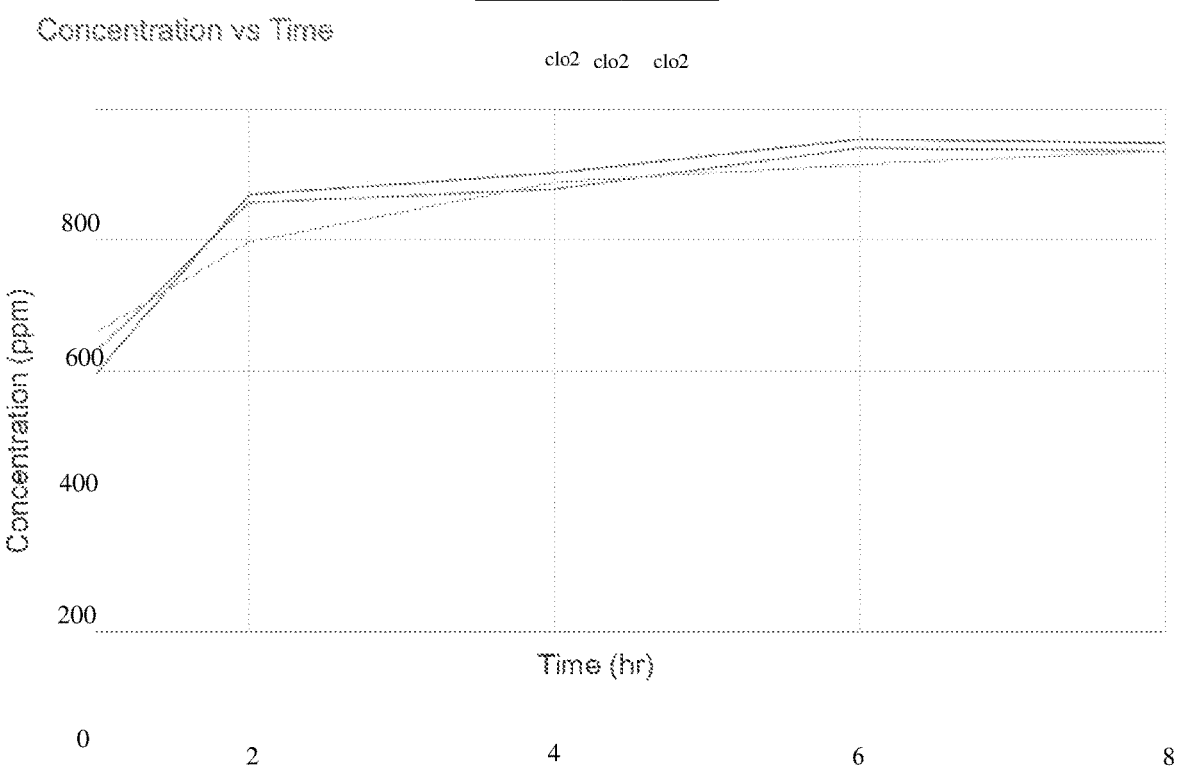
FIG. 10 is a graph depicting the concentration of a generated chlorine dioxide solution over time.

FIG. 10 is a graph depicting the concentration of a multiple generated chlorine dioxide solution over time. As can be seen in the graph, the concentration of each solution generated with the disclosed devices and methods remained stable over time.

Figure 11:
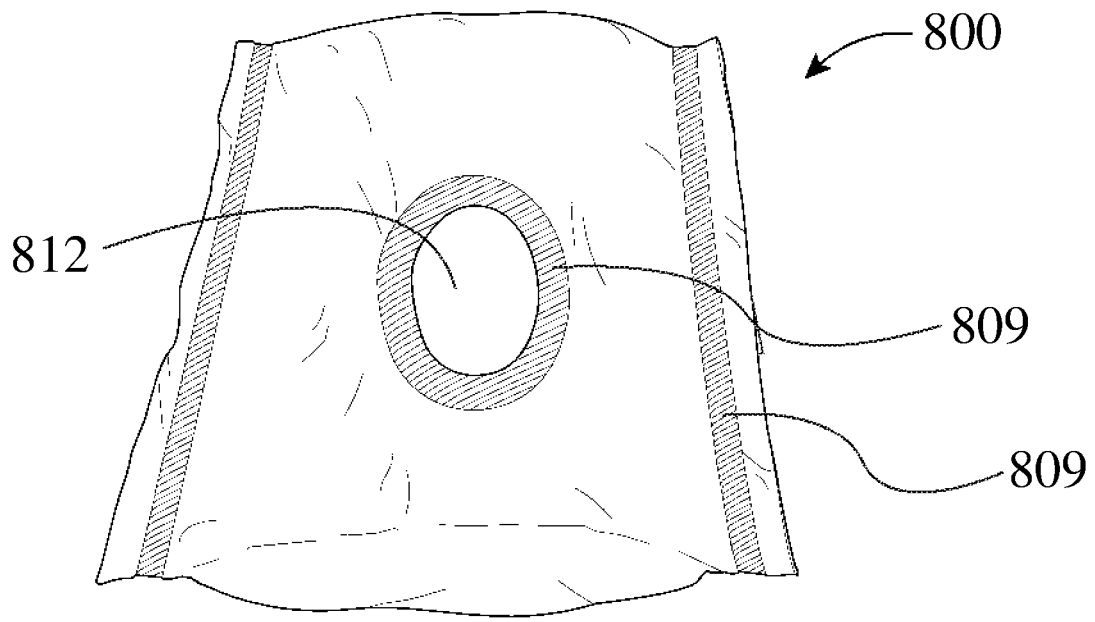
FIG. 11 is an outer view of a pouch for generating a gas having an opening, according to some embodiments.

FIG. 11 is an outer view of a pouch 800 for generating a gas having an opening 812, according to some embodiments. The opening 812 may be sufficiently large to allow for an object to pass through the pouch 800. For example, an anchoring element may pass through the opening 812 to secure the pouch 800 to a wall or surface. For example, one end of a locking mechanism may be inserted through the opening 812 and attached to another end of the locking mechanism, then locked to hold the pouch 800 in place.

The perimeter of the opening 812 may be sealed 809 to prevent passage of a reactant through the opening. The perimeter of the pouch 800 may be sealed 809 in a similar fashion. Examples of sealing may include stamping or heat sealing.

Figure 12:
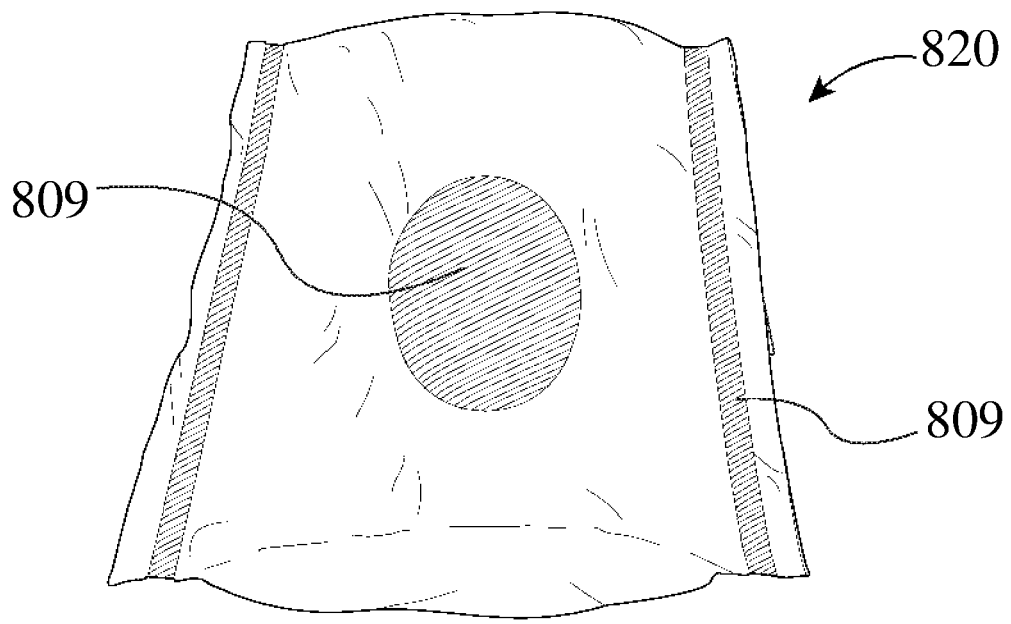
FIG. 12 is an outer view of a pouch having a central portion configured to attach to another object or surface, according to some embodiments.

FIG. 12 is an outer view of a pouch 820 having a central portion 811 configured to attach to another object or surface, according to some embodiments. The central portion 811 may have adhesive properties or may be physically attached to an object or surface. For example, the central portion 811 may allow the passage of a hook through the material of the central portion 811. Additionally or alternatively, the central portion 811 may be fastened to an object or surface comprised of similar material. Additionally or alternatively, the central portion may adhere to an object or surface via an adhesive compound. In some embodiments, the perimeter of the pouch 820 may be sealed 809.

Figure 13:
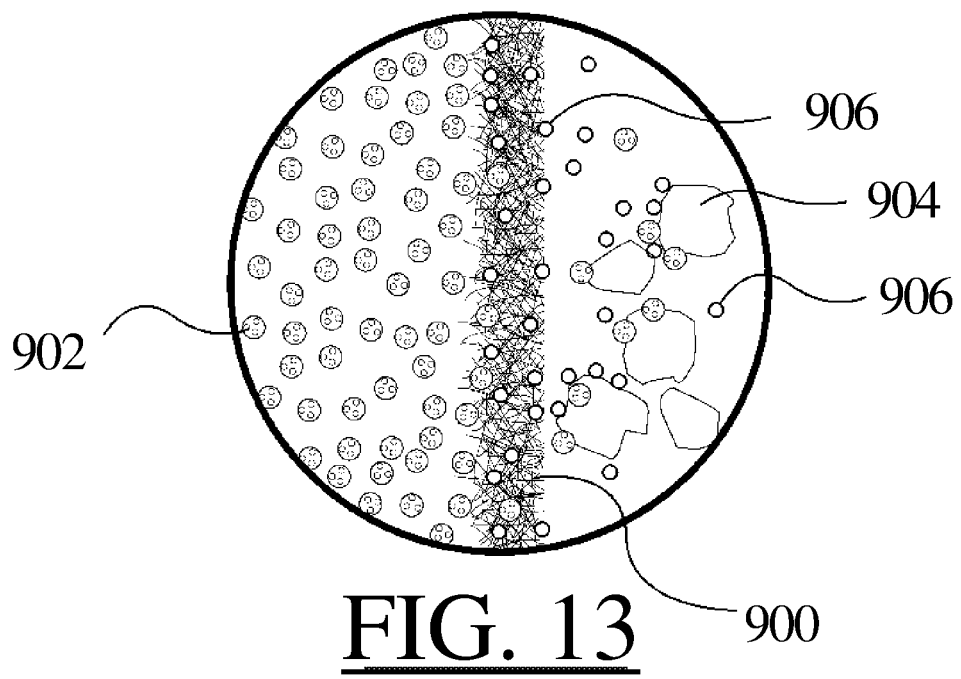
FIG. 13 is a mock-up microscopic view of moisture entering a pouch containing a reactant, according to some embodiments.

In some embodiments, the initiating agent is water vapor drawn from moisture in the air. FIG. 13 is a mock-up microscopic view of moisture 902 entering a pouch portion 900 containing a reactant 904, according to some embodiments. In environments of sufficient humidity, moisture 902 passes through the pouch portion 900. The moisture 902 then reacts with the reactant 904 within the pouch 900 to create a gas 906.

Figure 14:
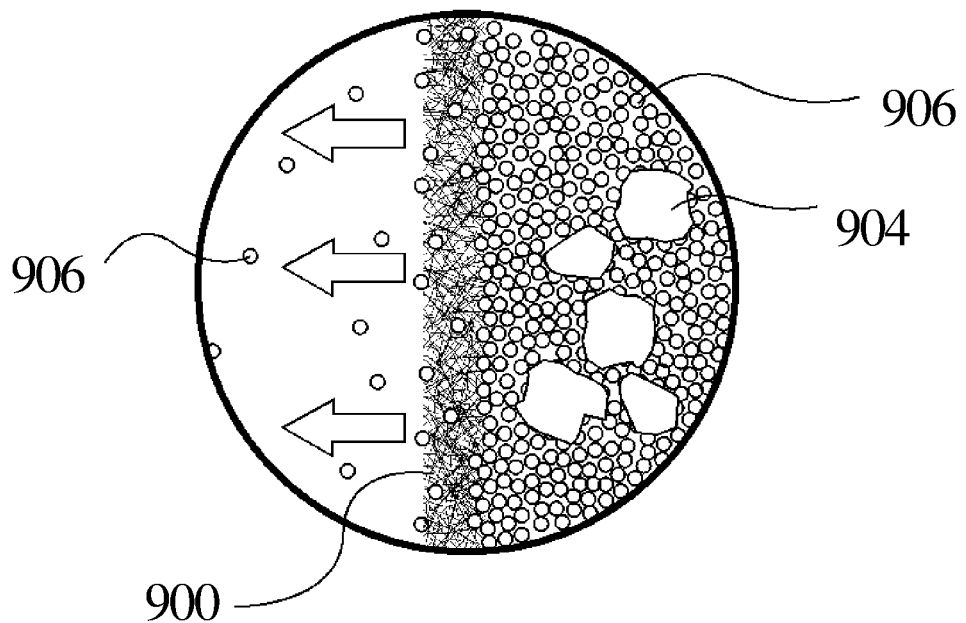
FIG. 14 is a mock-up microscopic view of a generated gas exiting a pouch containing a reactant, according to some embodiments.

FIG. 14 is a mock-up microscopic view of a generated gas 906 exiting a pouch portion 900 containing a reactant 904, according to some embodiments. As illustrated, the pouch portion 900 is composed of a sufficiently porous material to allow the passage of the generated gas 904, for example chlorine dioxide, carbon dioxide, oxygen, nitrogen, argon, helium, calcium carbonate, or a combination thereof. In some embodiments, a combination of carbon dioxide and chlorine dioxide is generated.

Figure 15:
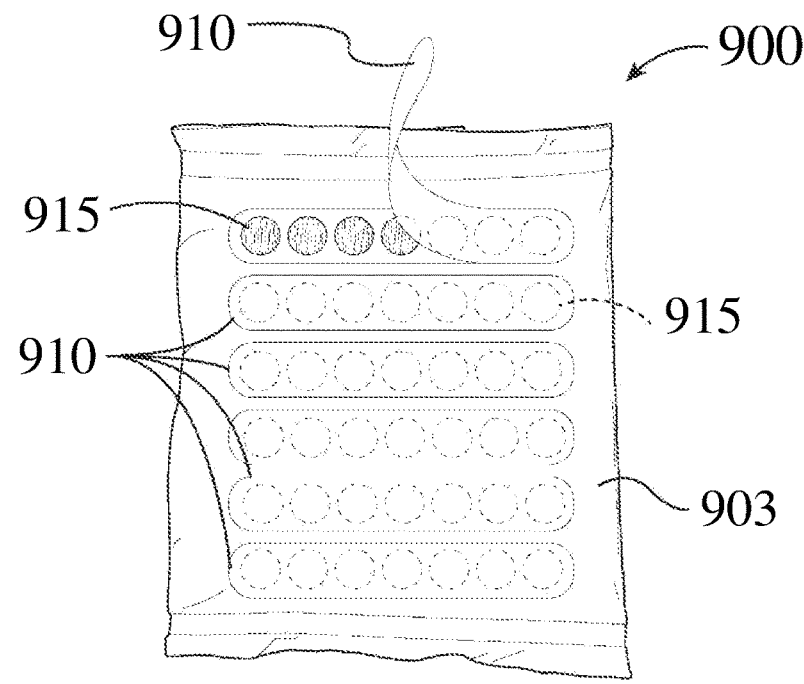
FIG. 15 is a front view of a pouch for generating a gas having removable sections to allow permeability of an initiating agent, according to some embodiments.

FIG. 15 is a front view of a pouch 900 for generating a gas having at least one removable section 910 to allow permeability of an initiating agent, according to some embodiments. In some embodiments, the removable sections 910 may be in the form of strips. A user may partially or fully remove a strip 910 to reveal one or more sections 915 that are permeable to moisture. The user may reveal more sections 915 to cause the production of greater amounts of gas as more reactant within the pouch 900 is exposed to moisture in the air.

In some embodiments, removable sections 910 may be detached from the pouch 900 via perforations. In other embodiments, removable sections 910 may be attached to pouch 900 with an adhesive.

In some embodiments, one or more portions 903 of pouch 900 are impermeable to air and moisture. Removable strips 910 are also impermeable to air and moisture.

Figure 16:
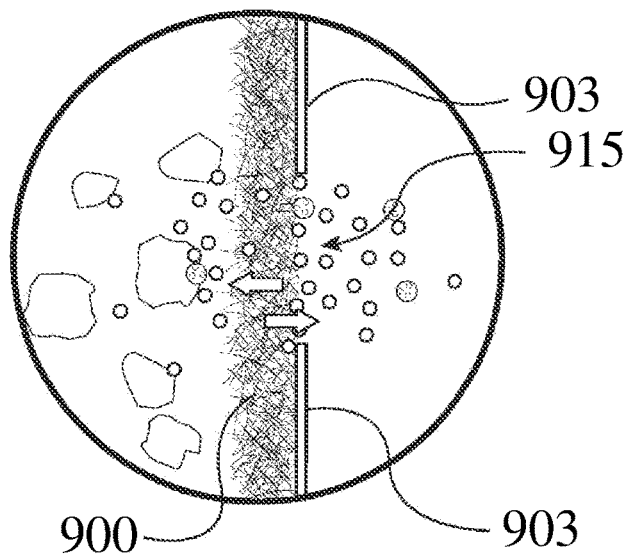
FIG. 16 is a mock-up microscopic view of a generated gas exiting the pouch of FIG. 15 after removal of a removable section, according to some embodiments.

FIG. 16 is a mock-up microscopic view of a generated gas exiting the pouch 900 of FIG. 15 after removal of a section, according to some embodiments. As illustrated, portions of the pouch 903 are impermeable to air and moisture. When a removable section 910 is removed, a section 915 is exposed to air and allows moistures to enter the pouch 900. The moisture mixes with the reactant to produce a gas.

Figure 17:
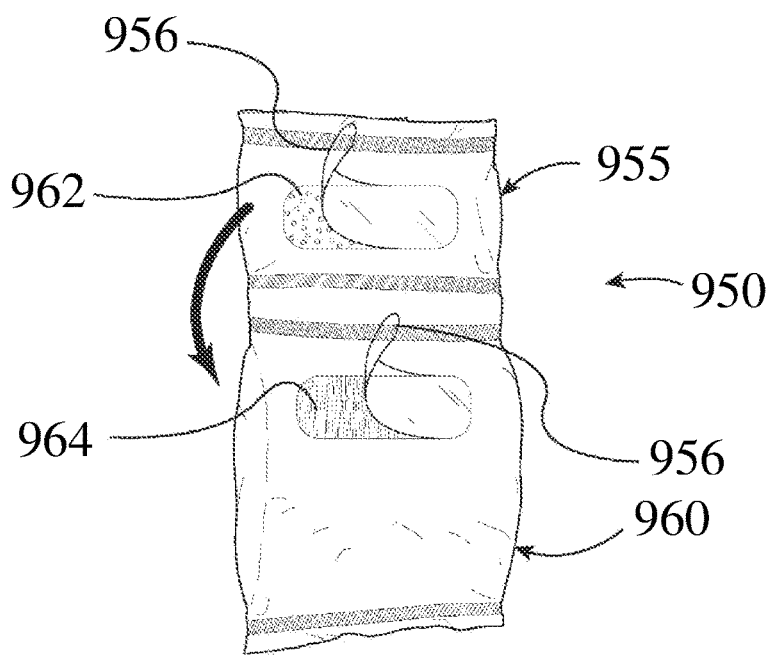
FIG. 17 is a front view of a dual pouch apparatus in an open configuration, according to some embodiments.

FIG. 17 is a front view of a dual pouch apparatus 950 in an open configuration, according to some embodiments. The dual pouch apparatus 950 may include an agent pouch 955 including an initiating agent 962 and a reactant pouch 960 including a reactant 964. In some embodiments, the agent pouch 955 and reactant pouch 960 both include at least one removable section 956. In some embodiments, removable sections 956 may be detached from a pouch via perforations. In other embodiments, removable sections 910 may be attached to a pouch with an adhesive. In some embodiments, the agent pouch 955 and reactant pouch 960 do not share an internal volume.

A user may remove a removable section 956 from agent pouch 955 to allow the initiating agent 962 to diffuse from the agent pouch 955. For example, removing section 956 from pouch 955 would allow water vapor to diffuse from the pouch 955. A user may remove a removable section 956 from the reactant pouch 960 to allow an initiating agent 962 to diffuse into the pouch 960 to react with the reactant 964.

In some embodiments, the user may place the initiating agent 962 into direct contact with the reactant 964. For example, the user may folder over the apparatus 950 to contact the agent pouch 955 to the reactant pouch 960. In some embodiments, the pouches are contacted at the areas that formerly included removable sections 956.

Figure 18:
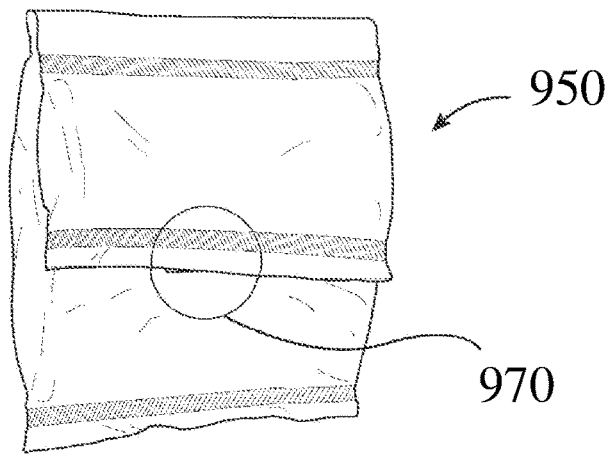
FIG. 18 is a front view of the dual pouch apparatus of FIG. 17 in a closed configuration, according to some embodiments.

When the agent 962 and reactant 964 are not in physical contact with one another, the apparatus 950 may be considered to be in an open configuration. When the agent 962 and reactant 964 are in physical contact with one another, the apparatus 950 may be considered to be in a closed configuration. FIG. 18 is a front view of the dual pouch apparatus 950 in a closed configuration, according to some embodiments. In some embodiments, agent pouch 955 and reactant pouch 960 include mated attachment features 970 to attach the two pouches. Attachment features 970 may include hook and loop fasteners, removable adhesives, snap fasteners, and the like.

Embodiments of the apparatus including agent pouch 955 and reactant pouch 960 may be useful in environments of low humidity. In such environments, the air would not contain sufficient moisture to produce a desired amount of gas when the reactant 964 is exposed to the air.

Figure 19:
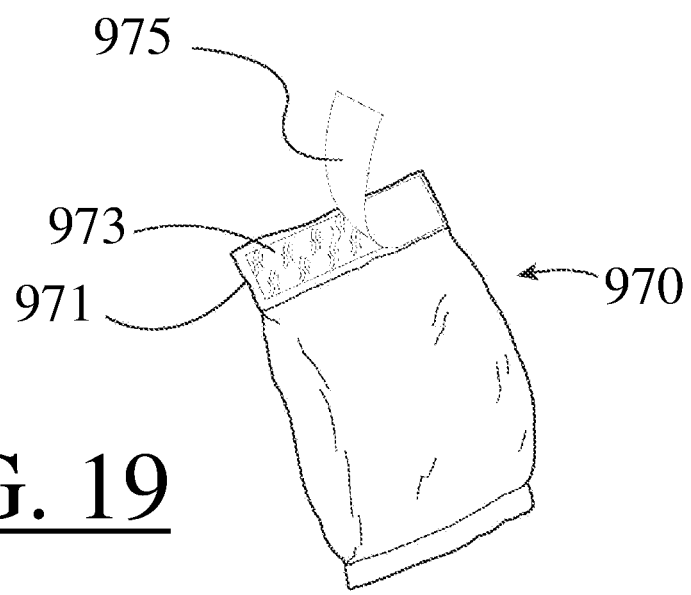
FIG. 19 is a front view of a pouch for generating a gas having an adhesive section, according to some embodiments.

FIG. 19 is a front view of a pouch 970 for generating a gas having an adhesive section 971, according to some embodiments. An adhesive section 971 may have a removable cover 975. Removal of the cover 975 exposes an adhesive 973. In some embodiments, the adhesive section 971 is located on at least a portion of a periphery of a pouch 970. In some embodiments, the adhesive section 971 is located on a portion of a surface of a pouch 970. In some embodiments, a pouch 970 includes multiple adhesive sections 971.

Figure 20:
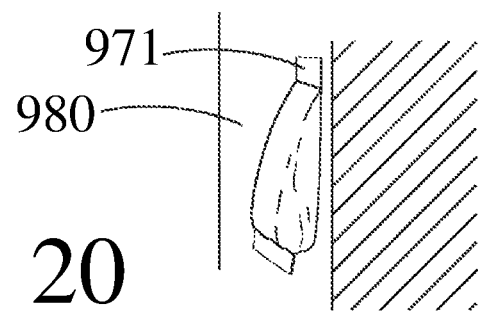
FIG. 20 is a side view of the pouch of FIG. 19 adhered to a surface, according to some embodiments.

FIG. 20 is a side view of the pouch 970 adhered to a surface 980, according to some embodiments. The pouch 970 is adhered to the surface 980 via the adhesive 973 on the adhesive section 971. Pouch 970 may be situated on a surface 980 such that a sufficient surface area of the pouch 970 is exposed to the air, allowing moisture from the air to enter the pouch 970 and generate a desired gas. In some embodiments, surface 980 is a wall, table, floor, or other flat surface.

The disclosed apparatuses and methods may be used to generate gases for a variety of uses. In some embodiments, chlorine dioxide is generated for use as a sterilizing agent. The generated chlorine dioxide may be collected and applied to a desired area. Alternatively, the apparatus may be placed in an area to be sterilized and the generated gas will sterilize nearby surfaces and objects. For example, the apparatus may be placed in a larger container with food that is to be sterilized.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

What is claimed is:

1. An apparatus for generation of a gas, comprising:
   a pouch consisting essentially of a single layer of polytetrafluoroethylene;
   a reactant disposed within an interior of the pouch and in direct contact with an interior lining of the pouch, wherein the reactant generates the gas in the presence of an initiating agent.

2. The apparatus of claim 1, wherein the layer of polytetrafluoroethylene comprises pores sized between 0.05 micrometers and 1.00 micrometers.

3. The apparatus of claim 1, wherein the layer of polytetrafluoroethylene comprises a bubble point ranging between 20 psi and 30 psi.

4. The apparatus of claim 1, wherein the initiating agent is water vapor.

5. The apparatus of claim 1, further comprising at least one pouch containing an initiating agent.

6. The apparatus of claim 1, wherein the reactant is a solid.

7. The apparatus of claim 1, wherein the reactant comprises a combination of sodium chloride and citric acid.

8. The apparatus of claim 1, wherein the reactant fills between 20-60% of the interior of the pouch.

9. The apparatus of claim 1, wherein the layer of polytetrafluoroethylene is configured to allow release of the gas out of the pouch.

10. The apparatus of claim 1, wherein the layer of polytetrafluoroethylene is configured to allow entry of the initiating agent into the interior of the pouch.

11. The apparatus of claim 1, wherein the interior of the pouch consists of the reactant and air.

12. The apparatus of claim 1, wherein the gas comprises at least one of chlorine dioxide, carbon dioxide, oxygen, nitrogen, argon, helium, or calcium carbonate.

13. The apparatus of claim 1, comprising multiple pouches connected in a manner that allows for removal of one pouch from the multiple pouches by cutting away the one pouch.

14. A method of forming an apparatus for generation of a gas, comprising,
   providing at least two pouches consisting essentially of a layer of polytetrafluoroethylene, each pouch comprising an interior, a reactant disposed within each interior, wherein the reactant generates the gas in the presence of an initiating agent;
   connecting the at least two pouches at a perimeter of each pouch, each pouch spaced from one another such that one pouch is removable from the at least two pouches by cutting away the one pouch.

15. The method of claim 14, wherein the at least two pouches are connected by heat sealing or stamping the perimeter of each pouch.

16. The method of claim 14, wherein the layer of polytetrafluoroethylene comprises pores sized between 0.05 micrometers and 1.00 micrometers.

17. The method of claim 14, wherein the layer of polytetrafluoroethylene comprises a bubble point ranging between 20 psi and 30 psi.

18. The method of claim 14, wherein the initiating agent is a vapor.

19. The method of claim 18, wherein the initiating agent is water vapor.

20. The method of claim 14, wherein the reactant is a solid.

21. The method of claim 14, wherein the reactant comprises a combination of sodium chloride and citric acid.

22. The method of claim 14, wherein the reactant fills between 20-60% of the interior of each pouch.

23. The method of claim 14, wherein the layer of polytetrafluoroethylene is configured to allow release of the gas out of each pouch.

24. The method of claim 14, wherein the layer of polytetrafluoroethylene is configured to allow entry of the initiating agent into the interior of each pouch.

25. The method of claim 14, wherein the interior of the pouch consists of the reactant and air.

26. The method of claim 14, wherein the gas comprises at least one of chlorine dioxide, carbon dioxide, oxygen, nitrogen, argon, helium, or calcium carbonate.

* * * * *